United States Patent [19]

SinghDeo et al.

[11] Patent Number: 4,883,778
[45] Date of Patent: * Nov. 28, 1989

[54] PRODUCTS FORMED OF A CERAMIC-GLASS-METAL COMPOSITE

[75] Inventors: Narendra N. SinghDeo, New Haven; Deepak Mahulikar, Meriden, both of Conn.; Sheldon H. Butt, Godfrey, Ill.

[73] Assignee: Olin Corporation, New Haven, Conn.

[*] Notice: The portion of the term of this patent subsequent to May 31, 2005 has been disclaimed.

[21] Appl. No.: 924,959

[22] Filed: Oct. 30, 1986

[51] Int. Cl.⁴ .................. C03C 8/18; C03C 14/00
[52] U.S. Cl. .................. 501/19; 123/193 C; 51/309; 623/16; 501/32
[58] Field of Search ............ 501/19, 32; 123/193 C; 51/309; 623/16

[56] References Cited

U.S. PATENT DOCUMENTS

| | | | |
|---|---|---|---|
| 4,018,717 | 4/1977 | Frencel | 501/19 |
| 4,293,325 | 10/1981 | Chirino et al. | 501/19 |
| 4,299,887 | 11/1981 | Howell | 501/19 |
| 4,323,484 | 4/1982 | Hettori et al. | 501/19 |
| 4,532,222 | 7/1930 | Butt | 501/32 |
| 4,561,996 | 12/1985 | Holmes | 501/19 |
| 4,569,692 | 2/1986 | Butt | 75/235 |
| 4,598,167 | 7/1986 | Ushifuss et al. | 501/19 |
| 4,659,404 | 4/1987 | Butt | 156/62.2 |
| 4,668,957 | 5/1987 | Spohr | 501/19 |
| 4,682,414 | 7/1987 | Butt | 29/840 |
| 4,748,136 | 5/1988 | Mahulikar et al. | 501/32 |

Primary Examiner—Mark L. Bell
Attorney, Agent, or Firm—Gregory S. Rosenblatt; Paul Weinstein

[57] ABSTRACT

The present invention is directed to an engineering ceramic product formed of a ceramic-glass-metal composite being strong, durable, formable into complex shapes and having good improved thermal conductivity.

15 Claims, 2 Drawing Sheets

PRODUCTS FORMED OF A CERAMIC-GLASS-METAL COMPOSITE

While the invention is subject to a wide range of applications, it is especially suited for use as an engineering ceramic adaptable for applications such as body prosthesis, engines, and cutting blades to name a few. The invention discloses a ceramic-glass-metal composite with a wide range of potential properties that may be specifically tailored according to the application.

This application relates to U.S. Pat. No. 4,569,692, entitled LOW THERMAL EXPANSIVITY AND HIGH THERMAL CONDUCTIVITY SUBSTRATE, by S. H. Butt; U.S. patent application Ser. No. 838,866, entitled CERMET SUBSTRATE WITH GLASS ADHESION COMPONENT, by D. Mahulikar; (now abandoned), U.S. Pat. No. 4,743,299 entitled CERMET SUBSTRATE WITH SPINEL ADHESION, by M. J. Pryor et al.; U.S. Pat. No. 4,748,136, entitled CERAMIC-GLASS-METAL COMPOSITE, by D. Mahulikar et al.; U.S. patent application Ser. No. 924,970, entitled ELECTRONIC PACKAGING OF COMPONENTS INCORPORATING A CERAMIC-GLASS-METAL COMPOSITE, by N. N SinghDeo et al.; U.S. patent application Ser. No. 707,636, entitled PIN GRID ARRAYS, by M. J. Pryor (now abandoned) and U.S. Pat. No. 4,715,892, entitled CERMET SUBSTRATE WITH GLASS ADHESION COMPONENT, by D. Mahulikar.

Throughout the world, fine ceramics are considered to be one of the most important basic materials for the 1990's and the 21st century. This expectation is based on the following factors. First of all, fine ceramics are expected to play an important role as a new basic material in developing and advancing such frontier industries as electronics, information technology, bio-technology, medical electronics, etc. The future of these industries depends on the development of new materials. They demand materials which have greater capability than any currently available material in resisting heat, corrosion, radioactivity, etc. They also demand new functional materials which show advanced performance in chemical, optical and electromagnetic functions. Fine ceramics are considered to be the materials which can fulfill these requirements and, hence, act as one of the key materials which will support the anticipated development of these frontier industries. Secondly, the excellent qualities of fine ceramics are expected to help existing industries improve the quality of their products. A ceramic engine for the car industry is just one example. Clearly, fine ceramics are expected to present great opportunity for currently depressed basic materials industries to revitalize themselves by becoming a supplier of fine ceramics. Thirdly, fine ceramics are considered to be important from the view of each country's national economic security. Every country is concerned about conserving its natural resources including oil and precious metals. Consequently, the development of a ceramic engine is eagerly awaited in order to conserve oil. The development of ceramics as a substitute for such precious metals as nickel, cobalt and chromium is similarly desired.

Presently, the main areas of application are electro-magnetic and mechanical components. The former is called electro-ceramics and includes IC packages, electrical condensers, thermistors and variable resistors. Mechanical and heat-resistance ceramics are called engineering ceramics and are conventionally used in applications such as gas turbines, turbo-charge turbines and ceramic engines. Informational electronics is one of the main areas where ceramics can be applied and where functional ceramics have already been used. Structural ceramics have been less widely applied in practice. However, they are expected to play an important role in improving the efficiency of energy uses in motor vehicles, industrial machinery and so on. Structural ceramics, also known as engineering ceramics, with their excellent mechanical and thermal capabilities are considered to be very important for the future. In addition, functional ceramics such as electrical ceramics and optical ceramics are expected to grow faster than ever in the wake of miniaturization and envelopment of new devices in the electronics industry. Bio-ceramics, such as those being used in artificial teeth and replacement joints, are also beginning to show rapid growth and will be spurred by the advancement of medical technology.

The disclosed invention provides a unique method of manufacturing ceramic bodies to their final configuration in fewer steps than possible by conventional means and at temperatures well below the firing temperature of either the conventional ceramics, i.e. about 1600° C., or even "low fired ceramics", i.e. about 900° C. The disclosed process also imparts unique properties to the manufactured product because organics are usually not required in the manufacturing process.

The innovative features of the present invention enable the composite to be effectively used in many areas of the growing ceramics industry. Even when the composite contains a large percentage of ceramic particles, it can now be die formed to a complex, final shape at moderate pressures and temperatures. The key to this discovery is the addition of a low concentration of metal or metal alloy particles which greatly reduces the range of forming pressures. In the past, the required high pressures primarily permitted only the forming of relatively non-complex configurations. With the metal or metal alloy particle additive, complex configurations with a tight tolerance are possible because the composite, at the processing temperature, flows quite readily. The forming technology is somewhat similar to that involved in injection molding of plastics. Presently, ceramic products having a complex shape are difficult to manufacture because of factors including the shrinkage and the hardness of ceramics. Once the ceramic product is formed to the general, final shape, is very time-consuming and expensive to machine it into the final design.

Even with this design limitation, ceramic materials have been employed in many products which take advantage of their high strength, chemical durability and light weight. For example, ceramics have been incorporated in engines, artificial limbs, and cutting tools to name just a few.

It is a problem underlying the present invention to manufacture engineering ceramic products of a ceramic-glass-metal composite whose physical characteristics can be tailored to provide specific mechanical, electrical, thermal, and chemical properties.

It is an advantage of the present invention to provide engineering ceramic products formed of a ceramic-glass-metal composite which obviates one or more of the limitations and disadvantages of the described prior arrangements.

It is a further advantage of the present invention that engineering ceramic products formed of a ceramic-glass-metal composite which can be molded into complex shapes are provided.

It is a still further advantage of the present invention that engineering ceramic products formed of a ceramic-glass-metal composite which can be molded into components with a tight tolerance are provided.

It is another advantage of the present invention that engineering ceramic products formed of a ceramic-glass-metal composite which can be fired at a low temperature are provided.

It is yet another advantage of the present invention that engineering ceramic products formed of a ceramic-glass-metal composite which can be inexpensively processed are provided.

Accordingly, there has been provided engineering ceramic products formed of a ceramic-glass-metal composite. These products are strong, durable, formable into complex shapes and have improved thermal conductivity. They include rotors, engine blocks, replacement for body parts, and grinding wheels to name a few. The ceramic-glass-metal composite includes ceramic particles, a glass for adhering the ceramic particles together and metallic particles to enhance the flow characteristics at a processing temperature.

The invention and further developments of the invention are now elucidated by means of the preferred embodiments in the drawings.

DETAILED DESCRIPTION OF THE DRAWINGS

Figure 1:
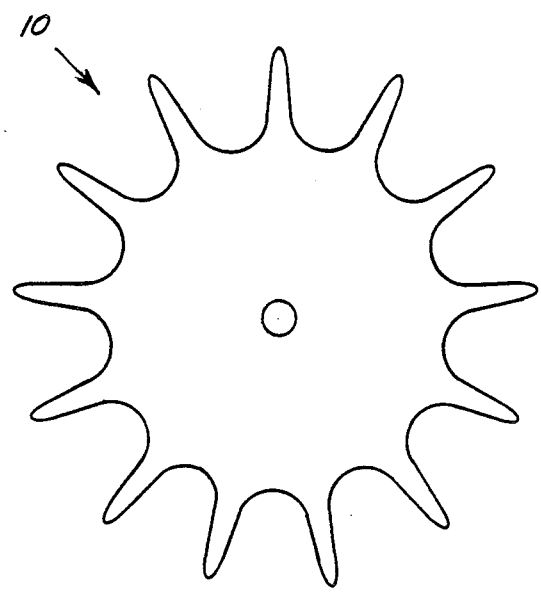
FIG. 1 is a perspective view of a ceramic rotor for a turbo-charge turbine.

This invention is directed to ceramic articles that are easily formed with selected compositions depending upon the specific application. The disclosed composite is particularly advantageous for use in the general area of engineering ceramics. This includes a wide range of new applications for ceramics in areas such as ceramic engines and engine parts, cutting tools, body replacement parts and a wide variety of other possibilities. The invention is particularly useful to form products which both require the advantages inherent in a ceramic material as well as the need for close tolerances and ease of manufacture. The ceramic materials are particularly noted for their ability to withstand high temperatures, their low dielectric constant, their high strength, and their chemical stability.

The present invention particularly relates to a composite formed of a mixture of ceramic and metallic particles adhered together by a glass. The composite can be hot forged, hot pressed or cast into any desired shape at the processing temperature where the selected glass is in the fluid condition, the metallic particles are ductile and in the solid condition, and the ceramic particles are in the solid condition. The result is a precisely shaped product having desired physical characteristics.

The invention involves mixing together appropriate proportions of at least three different types of materials to provide selected properties. One of the materials is a ceramic powder which is present in a volume percent range selected according to the desired physical property requirements such as the mechanical, electrical, thermal and chemical properties. Typically, ceramics are known for their physical characteristics including high strength, low ductility, high dielectric constant, low coefficient of thermal expansion and chemical non-reactivity. The second material is a glass which forms a matrix for binding the ceramic and metallic particles together. Since glass is relatively fragile, it is typically provided at such a proportion so as to prevent a significant reduction of the composite strength, primarily provided by the ceramic particles. The glass is selected to be chemically reactive with the ceramic particles as well as with the third material, a metal or alloy. The third material is comprised of metal or alloy particles which are dispersed throughout the composite. The metal or alloy particles enable the ceramic particles to shift position, while the composite is being pressed into a desired shape at the processing temperature, with less applied pressure as compared to a ceramic-glass slurry alone. In addition, the metal particles improve the thermal conductivity of the composite. The metal particles are preferably soft and ductile. It is believed that they tend to mold onto the adjacently disposed surfaces between adjacent ceramic particles so that the ceramic particles can slide over each other during the forming process without being damaged. It is believed that the metal particles substantially reduce the occurrence of interlocking between ceramic particles thereby reducing the pressure necessary for forming the final shapes. The resulting composite is particularly useful in that it may be readily formed by a one step process into a complex, final shape having a very tight tolerance.

The ceramic material typically comprises particles selected for their physical characteristics. The specific ceramic may be selected from the group consisting of $Al_2O_3$, SiC, BeO, $TiO_2$, $ZrO_2$, MgO, AlN, $Si_3N_4$, BN and mixtures thereof. The present invention is not limited to these ceramics and may incorporate any desired ceramic or mixture of ceramics. The ceramic particles are present in a range of from about 20 to about 80 volume percent of the final fired composite and in a preferred range of from about 40 to about 65 volume percent. The ceramic particles can have any desired shape and have an average diameter of over about 1 micron, preferably, between about 1 to about 200 microns and most preferably, between about 40 to about 100 microns. The factors considered in selecting the desired ceramic include its dielectric constant, its coefficient of thermal expansion, its strength and chemical durability.

Conventionally, ceramics have been chosen for their high temperature capabilities since their melting point is at a temperature between about 1300° to about 2500° C. However, the present invention may not require the high temperature capabilities since the ceramic particles are bonded together in a glassy matrix which may have a relatively low softening temperature as compared to that of he ceramic. It is also within the terms of present invention to choose glasses which can be frabricated into components that are stable at very high temperatures.

A second component of the composite comprises a glassy phase having any desired composition in accordance with the properties required by the final composite. The glassy phase functions to bind the ceramic and metallic particles together within a matrix of the glass. An important characteristic is that the glass preferably is chemically reactive with both the ceramic and metallic components. Also, it may be important that the glass has physical characteristics such as good chemical durability, high strength, an acceptable dielectric constant, and a softening point in a selected temperature range. Suitable glasses may be selected from the group consisting of silicate, borosilicate, phosphate, zinc-borosilicate, soda-lime-silica, lead-silicate, lead-zinc-borate glasses, however, any desired glass may be utilized. They may include phosphate glass systems having high coefficients of thermal expansion and relatively low temperature softening points. In addition, a vitreous or devitrified glass may be selected.

A preferred example of a useful glass which provides thermosetting properties suitable for application in an electronic environment is a devitrified, solder glass. This glass is a $PbO-ZnO-B_2O_3$ type glass and has a nominal composition of about 10 wt. % $B_2O_3$, 0.025 wt. % $Al_2O_3$, 8.5 wt. % $SiO_2$, 0.04 wt. % $TiO_2$, 0.01 wt. % $Fe_2O_3$, 8.5 wt. % ZnO, 12.5 wt. % $ZrO_2$, 0.25 wt. % $HfO_2$, 2.0 wt. % $BaO_2$ and the balance PbO. After the glass is liquid, it is held at a temperature of about 500° C. for about 10 minutes. The glass, upon solidification, then devitrifies. At that point, it will not remelt until it reaches a temperature of about 650° C. The glass is present in a range of from about 15 to about 50 volume percent of the fired composite and in a preferred range of from about 20 to about 40 volume percent. The glass is preferably selected with a softening temperature of from about 300° to about 1300° C. The processing temperature is selected so that the glass is at least above its softening point and preferably is in the liquid state.

A thermosetting composite may be formed by mixing ceramic and metal particles with a glass that devitrifies above a certain temperature. First, the composite is preferably formed at a processing temperature where the glass is in a liquid condition. The composite may then be held in an oven at approximately the processing temperature for a sufficient period so that it has a devitrified structure when it solidifies. When the glass is in the crystalline state, it is usually much stronger than in the vitreous state. A composite of this nature, i.e. ceramic and metal particles mixed with a devitrified glass, may be characterized as a thermosetting material. The latter characteristic is imparted because the remelting temperature is considerably higher than the original processing temperature.

For example, a devitrifiable solder glass, CVIII manufactured by Owens Illinois Co., becomes liquid at a processing temperature of about 470° C. This glass as previously described is a $PbO-ZnO-B_2O_3$ type glass and has a nominal composition of about 10 wt. % $B_2O_3$, 0.025 wt. % $Al_2O_3$, 8.5 wt. % $SiO_2$, 0.04 wt. % $TiO_2$, 0.01 wt. % $Fe_2O_3$, 8.5 wt. % ZnO, 12.5 wt. % $ZrO_2$, 0.25 wt. % $HfO_2$, 2.0 wt. % $BaO_2$ and the balance PbO. After the glass is liquid, it is held at a temperature of about 500° C. for about 10 minutes so that upon solidification it has a devitrified structure. At that point, it will not remelt until it reaches a temperature of about 50° C. The thermosetting characteristics of the devitrified glasses are particularly advantageous because they allow the final product to be used in a higher temperature environment than the original processing temperature.

The third component of the composite comprises metallic particles which preferably are ductile at the processing temperature. The metallic particles are provided for their ability to reduce significantly the pressure necessary to densify the final composite product. It is believed that they mold about the surfaces of the ceramic particles when they are pressed between the ceramic particles during the processing procedures, thereby reducing or eliminating interlocking of the ceramic particles so as to reduce processing pressures. For example, the usual processing includes heating the mixture of ceramic particles with the metallic particles and the glass to the processing temperature where the metal particles are soft and ductile but not molten. The resulting composite slurry may be formed, i.e. in a mold. As the ceramic-glass-metal slurry flows into the shape of the mold, the ceramic particles are pressed against each other. The glassy phase is squeezed out from between adjacent ceramic particles providing points of contact. Without the presence of the metallic particles, the ceramic particles would remain in contact and could lock in position thereby retarding the ability of the slurry to flow. The ease of flowability is required for densification and shaping of the composite to the desired final configuration. Any loss of flowability becomes increasingly significant as the final shape becomes more complex.

A unique aspect of the present invention is the addition of metallic particles into the composite to significantly affect the flowability of the composite slurry. The metallic particles act sort of as a lubricant to enable the ceramic particles to slide over each other. It is believed that some of the metallic particles move into the interstices between adjacent ceramic particles and mold onto the ceramic particles at the points of contact which could interlock. It is believed that the metallic particles, being squeezed by the ceramic particles moving towards each other, adhere to the ceramic particles and then deform. This deformation enables the slurry containing the ceramic particles to move and flow, i.e. in a mold, while preventing damage to the ceramic particles.

The metallic particles may be constituted of any metal or alloy which does not melt at the processing temperature of the composite. Preferably, the metals and alloys are selected from the group consisting of aluminum, copper, iron, silver, gold, stainless steel and alloys thereof. Preferably, the selected metals and alloys are ductile at the processing temperature. Since any metal or alloy is ductile slightly below its melting temperature and below its solidus, respectively, a suitably selected processing temperature enables the use of any metal or alloy which will be ductile at the latter temperature. In the case where the metal or alloy is not ductile enough at the processing temperature, added pressure may be applied during the forming process to provide the required deformation. The metal or metal alloy particles preferably have an average diameter between about 0.01 to about 50 microns.

The final, fired composite may either contain the metallic particles dispersed continuously or discontinuously throughout the composite. Even in the case where the metallic particles are dispersed continuously, they do not form a matrix and are primarily subject to localized sintering. When the particles are dispersed continuously, the product would be classified as electrically conductive and when the particles are dispersed discontinuously the product would typically be classified as an insulator.

The metallic particles are present in the composite in an effective amount up to about 45 vol. % of the fired composite to enhance the flow characteristics of the composite at the processing temperature. Preferably, the metallic particles make up from about 5 to about 45 vol. % of the composite.

For applications where the composite is preferably classified as an insulator such as for electronic packaging components, the metallic particles are preferably provided in a volume percent so that they are discontinuously dispersed throughout the fired composite. Preferably, the metal or metal alloy particles in this instance make up less than about 25 volume percent of the final, fired composite. More preferably, the metal particles make up less than about 15 volume percent of the fired composite. Limiting the volume percent of metallic particles within these ranges is believed to prevent the formation of a continuous metal path in the final, fired composite.

The final composite, even with discontinuously dispersed metallic particles, exhibits improved thermal conductivity as compared with a composite formed with only ceramic particles bonded together with a glassy matrix. It is particularly surprising that the final composite having dispersed metallic particles has increased thermal conductivity since there is no corresponding increase in electrical conductivity. The reason for this unusual characteristic is not fully understood.

The process of forming the composite of the present invention includes providing three primary components; ceramic particles, metallic particles and a glass. The process may be accomplished by different techniques depending on the specific materials selected. For example, the ceramic particles may first be mixed with relatively ductile metal particles. Next, glass particles for bonding the ceramic particles together are added to the mixture. The mixture is heated to the processing temperature preferably corresponding to the temperature at which the glass particles are liquid and at least to their softening temperature. This preferably provides a semi-solid slurry of molten glass with solid metal and ceramic particles dispersed therein. Then, the composite preferably as a semi-solid slurry can be formed by conventional processes such as hot forging or hot pressing in a mold to any desired shape. With hot pressing, the mixture is preferably compacted at a pressure of from about 500 pounds per square inch (psi) to about $300 \times 10^3$ psi. The lowest usable pressure is believed to be that which enables the metallic particles, adhered between adjacent ceramic particles, to deform. This depends on the ductility of the metal or alloy at the processing temperature. In the event that the metal is not ductile enough at the processing temperature, a higher pressure may be used to deform the metal particles.

Finally, the mixture is cooled to solidify the glass and bind the composite into a final devitrified shape. A conventional parting agent, such as boron nitride, may be provided on the mold walls to enhance the removal of the pressed product from the mold. Preferably, the parting agent does not stick to either the mold walls or the pressed body. However, the primary consideration is that the parting agent does not stick to the mold walls. An important advantage of the present invention is that the pressed composite is very dense and has a final shape that very closely corresponds to that of the mold.

The present invention can produce parts with much tighter tolerance, and a more complex shape than ceramic manufacturing processes currently available in the industry. This significant advantage is primarily due to the following reasons. Firstly, the starting materials do not necessarily contain any constituents, such as organics, which are lost during the actual process of fabrication. These losses can result in undue shrinkage. Secondly, the metal particles enable the ceramic particles to better flow over each other during processing. Another important advantage is that the firing temperature may be substantially lower than the range of temperatures at which ceramic materials are now fired. Processing at a lower temperature inherently decreases the processing cost as compared to any known process.

The fabrication process may include conventional steps including hot pressing, hot forging and casting. Hot pressing can be carried out directly on the mixture of powders or on cold compacts. Depending on the glass, however, the hot pressing may require oxidizing atmospheres. For example, a solder glass such as PbO-ZnO-$B_2O_3$ requires an oxidizing atmosphere to prevent a change in the state of the glass.

Additional improvements in both thermal and mechanical properties can be obtained by using devitrified glasses in the composite. For electronic packaging, a devitrified glass enables the package to be formed at a significantly lower temperature than the temperature at which the package will operate.

An important aspect of the present invention is the ability to embed metallic elements, of any desired shape, into the composite. This can be accomplished in a single step during the hot pressing of the composite into a final shape. The metallic element is preferably formed of any metal or alloy which is thermally compatible with the glassy phase in the composite. If the metallic element does not adhere to the glassy phase, it may be appropriate to place an adherent coating on the surface of the metallic element to accomplish the same purpose. Examples of suitable metals include the group consisting of nickel, copper, aluminum, iron, gold, silver and alloys thereof.

Figure 3:
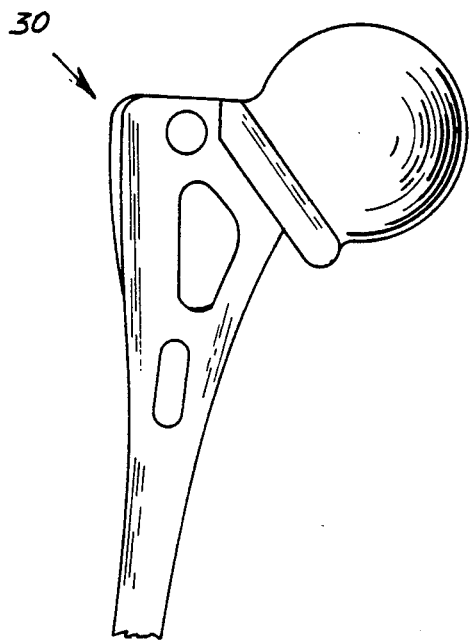
FIG. 3 is a perspective view of a hip and leg bone prosthesis.
Figure 2:
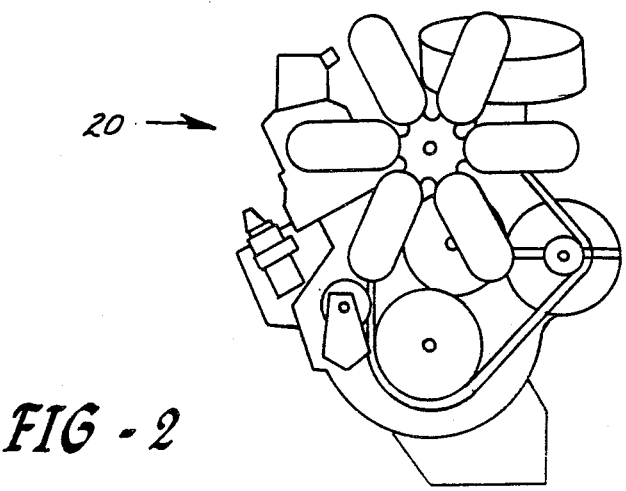
FIG. 2 is a perspective view of a ceramic engine.
Figure 4:
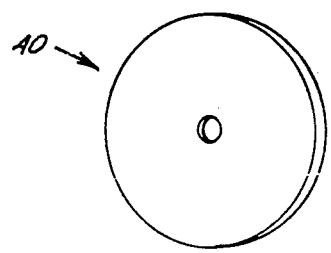
FIG. 4 is a perspective view of a grinding wheel.
Figure 5:
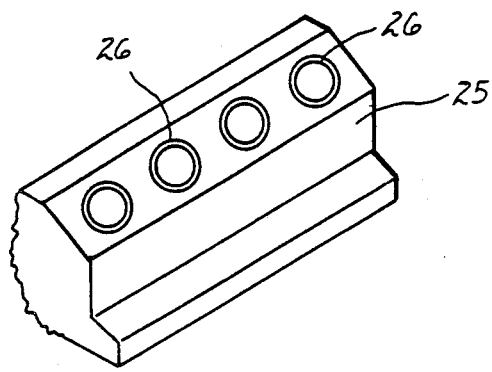
FIG. 5 is a perspective view of a ceramic engine block.

FIGS. 1 through 5 show a variety of articles which may be formed of the composite of the present invention. FIG. 1 is an example of ceramic rotor blade; FIG. 2 is an example of an engine formed of primarily ceramic parts; FIG. 3 is an example of a body part prosthesis; FIG. 4 is an example of a grinding wheel; and FIG. 5 is an example of a ceramic engine block with metal inserts; all formed of the composite in accordance with this invention. The examples shown in FIGS. 1 through 5 are not meant to be exhaustive of the possible uses of the disclosed composite but rather exemplifies the broad range of its use. Typically, the composite of this invention is most useful in applications where the physical characteristics of a ceramic are particularly advantageous.

The specific structure shown in FIGS. 1 through 5 are merely exemplary and are not meant to be limitive of the invention. Rather, each figure represents an example of the type of article in accordance with this invention. The structural shape shown are indeed well-known structural shapes and a wide variety of other well-known structural shapes could be employed in their place to provide the same type of articles.

In accordance with this invention, it is preferred to form the articles from a mixture of the ceramic-glass-metal composite by conventional processes including hot forging and hot pressing in a mold. Alternatively, if desired, the composite may be preformed and held together with an organic, such as, for example, polymethylmetacrylate (PMMA) polyvinylalcholol (PVA). In processing, the preform is first heated and held at a temperature and time whereby the volatilize organics are removed. Then, the preform may be hot pressed or hot formed so that the maximum density can be achieved in the final product.

FIG. 1 illustrates a ceramic rotor 10 fabricated from the ceramic-glass-metal composite. For a number of years, there has been an attempt to improve the efficiency of turbo-charge turbines for engines by using ceramic components in areas exposed to high temperature exhaust. This is important for future generations of gas engines to be smaller and more efficient. Uncooled metal super alloys, which are presently used in turbo-charge turbines and particular for the rotors, will not perform adequately at these temperatures due to creep related failures. In addition, the rotors are in constant contact with highly corrosive, high temperature engine exhaust gases. Moreover, the fabricating of a rotor is very demanding because of its complex shape. Attempts have been made to replace the expensive super alloy turbine blades with ceramic blades. However, the processing is very expensive and not amenable to mass production. Due to the strength of the ceramic material, the final shaping requires expensive and time-consuming cutting with a material such as a diamond. A ceramic rotor, using the principles of the present invention, can be manufactured at a reasonable cost since it can be formed, in a one step process, into a precision, complex shape. Both the metal particles and the glass of the composite are preferably selected to withstand the operating temperatures experienced by the ceramic rotor. For example, the glass might be selected from a borosilicate which has a liquid temperature of about 1220° C. The metallic particles are preferably corrosion resistant and can be selected from materials such as stainless steel, tungsten, molybdenum and nickel. The ceramic is selected to be able to withstand the temperatures and chemical properties of the gases. These include alumina, silicon-carbide and titanium-carbide. It is believed that the present invention provides an unusual opportunity to mold the ceramic rotor into its required complex curved shape due to the substantial elimination of skrinkage problems as was prevalent in the prior art. It is also believed that the present invention enables the fabrication of a ceramic rotor at a lower price, a lower temperature and with a significantly better shape tolerance.

FIG. 2 illustrates an engine 20 having many components fabricated of the ceramic-glass-metal composite. The composite material is particularly advantageous for forming engine blocks since it can withstand a high operating temperature, is easily formed into precise, complex shapes and comprises relatively inexpensive materials. Moreover, if desired, metal inserts may be molded directly into the composite when it is formed, as required. It is thought that engines, primarily formed of ceramics, are particularly useful since they can operate at much higher temperatures than metal engines and possibly eliminate the need for cooling.

The engine block 25 illustrated in FIG. 5 may be formed of the ceramic-glass-metal composite. Metal inserts, such as the cylinders 26, may be incorporated in the engine bloc as appropriate. The ceramic-glass-metal composite suitable for an engine block may comprise about 20 to about 35 volume percent of a borosilicate glass, from about 5 to about 10 volume percent of iron or iron alloy particles and the remainder alumina particles. Moreover, the constituents of the composite can be selected in a proportion so that the material has a high thermal conductivity to further enhance the cooling of the engine block. This might include increasing the volume percent of iron or iron alloy particles to about 30 to about 40 volume percent so that they are in a continuous dispersion throughout the composite. In this case, the glass would most likely be present in a range of from about 15 to about 25 volume percent.

FIG. 3 shows a replacement body part 30. In particular, this is a human hip prosthesis. In the past, human body parts and in particular bones and joints have been formed from ceramics as well as stainless steel and titanium and cobalt alloys. The metallic materials are particularly susceptible to corrosive fatigue since they reside in a biological atmosphere. The needed physical properties of a bone replacement is toughness, non-corrosiveness and ease of formability. The composite material of the present invention is particularly advantageous for this application. Appropriate materials and proportions can be selected so that the composite is easy to form into a complex shape, non-corrosive and somewhat similar and, therefore, compatible to human bones, thus rapid adaptation to the human body. It is thought that a suitable composite might be formed of about 40 to about 65 volume percent of a ceramic such as alumina. Alumina is particularly advantageous because of the high quality in which it may be obtained. The metallic particles are preferably selected to be highly resistant to corrosion and may include silver, gold or stainless steel. Metallic particles will make up about 5 to about 15 volume percent of the final composite. The remainder of the composite is of a glass which is thought to have good chemical durability in a human body at the body temperature. In this application, the composite is particularly advantageous because of the ease of forming the complex shapes required, the chemical durability and the ability to change the shape as required. This is particularly important for replacement parts since they must be custom made to a doctor's specifications. Although, a hip prosthesis is illustrated, it is within the terms of the present invention to form any desired body part as required.

FIG. 4 illustrates a grinding wheel 40. One important characteristic of a grinding wheel is its hardness so that it may cut many other materials. Also, wear resistance is a factor regarding its life expectancy. The wheel is preferably brittle so the particles will come off and provide a new cutting surface. Heat dissipation is also important and, finally, the wheel should be thermal shock resistant. The ceramic-glass-metal composite of the present invention may be readily formed into a grinding wheel having each of these characteristics. The metallic particles make up about 5 to about 20 volume percent of the composite and are selected from materials including copper, tungsten, molybdenum, nickel and alloys thereof. The glass makes up about 15 to about 25 volume percent of the composite and is preferably a borosilicate. The remainder of the composite is a ceramic and may be selected from materials including alumina, silicon-carbide and titanium-carbide. The metal particles, being dispersed throughout the wheel, provide a high thermal conductivity and enable good heat transfer from the wheel.

FIGS. 1 through 5, therefore, illustrate a wide variety of engineering ceramic products which can be formed of the composites in accordance with this invention. While specific materials were mentioned with respect to the various articles, they were meant to be exemplary and not limitive of the invention. Any desired ceramic-glass-metal composite in accordance with this invention could be employed in any of the articles shown. Other uses of the disclosed ceramic-glass-metal composite include cutting tools, seals, bearings, scissors, and knives.

In summary, these articles are provided in accordance with this invention having high strength, easy formability into complex shapes with tight tolerance and corrosion resistance.

Although the present invention is described in terms of hot pressure forming, it is also within the terms of the present invention to form the ceramic-glass-metal composite using other techniques such, as those employed in glass manufacture, including casting, blow casting and blowing.

For the purpose of this invention, a final, fired composite is defined as the composite after densification at the processing temperature. Discontinuously dispersed means that the particles are not generally interconnected so as to provide electrical conductivity. Continuously dispersed means that the particles are generally interconnected to provide electrical conductivity. Engineering ceramics include all fine ceramics mixed with other materials as required, i.e. the ceramic-glass-metal composite of the present invention, which are used in areas including electro-ceramics, mechanical and heat-resistance ceramics, functional ceramics, structural ceramics, bio-ceramics, electrical ceramics and optical ceramics.

The patent and patent applications set forth in this application are intended to be incorporated in their entireties by reference herein.

It is apparent that there has been provided in accordance with this invention products formed of a ceramic-glass-metal composite adapted for use as an engineered ceramic which satisfies the objects, means and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications and all variations as fall within the spirit and broad scope of the appended claims.

We claim:

1. An engineering ceramic product formed from a ceramic-glass-metal composite, comprising:
    from about 5 to about 45 volume percent of metallic particles for enhancing the flow characteristics of said composite, said metallic particles selected from the group consisting of aluminum, copper, iron, silver, gold, stainless steel and alloys thereof;
    from about 15 to about 50 volume percent of a glass for adhering said composite together; and
    the balance essentially ceramic particles, said ceramic particles selected from the group consisting of $Al_2O_3$, SiC, BeO, $TiO_2$, $ZrO_2$, MgO, AlN, $Si_3N_4$, BN and mixtures thereof;
    said composite having a structure comprising substantially a matrix of said glass with said ceramic and metallic particles dispersed therein.

2. The product of claim 1 which comprises a ceramic rotor.

3. The product of claim 2 including said ceramic particles being alumina;
    said glass being a borosilicate; and
    said metallic particles being an iron or iron alloy.

4. The product of claim 3 wherein said glass comprises about 20 to about 35 volume percent of said composite, said metal comprises about 5 to about 10 volume percent of said composite and the balance essentially ceramic particles.

5. The product of claim 1 which comprises a ceramic engine block.

6. The product of claim 5 wherein said ceramic engine block includes metal inserts incorporated therein.

7. The product of claim 6 wherein said metal inserts form cylinders.

8. The product of claim 5 including said ceramic particles being alumina;
    said glass being a borosilicate; and
    said metallic particles being an iron or iron alloy.

9. The product of claim 8 wherein said glass comprises about 20 to about 35 volume percent of said composite, said metal comprises about 5 to about 10 volume percent of said composite and the balance essentially ceramic particles.

10. The product of claim 1 which comprises a body prosthesis.

11. The product of claim 10 wherein said metal particles are selected from the group consisting of silver, gold, stainless steel and alloys thereof; and the ceramic is alumina particles.

12. The product of claim 11 including said metal being from about 5 to about 15 volume percent of said composite, said ceramic particles being about 40 to about 65 volume percent of said composite and the balance essentially glass.

13. The product as in claim 1 which comprises a grinding wheel.

14. The product of claim 13 including said ceramic particles being selected from the group consisting of alumina, silicon-carbide and titanium-carbide; the metal selected from the group consisting of copper, nickel, tungsten and molybdenum; and the glass being a borosilicate.

15. The product of claim 14 including said metal particles being about 5 to about 20 volume percent of the composite, the glass being about 20 to about 25 volume percent of the composite and the remainder being the ceramic particles.

* * * * *